US011459182B1

(12) United States Patent
Alamri

(10) Patent No.: US 11,459,182 B1
(45) Date of Patent: Oct. 4, 2022

(54) RELATIVE-PERMITTIVITY-BASED ONLINE MONITORING SYSTEM FOR SCREW CONVEYORS

(71) Applicant: Saudi Arabian Oil Company, Dhahran (SA)

(72) Inventor: Abdulrahim Y. Alamri, Khobar (SA)

(73) Assignee: Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 17/237,563

(22) Filed: Apr. 22, 2021

(51) Int. Cl.
*B65G 43/02* (2006.01)
*B65G 33/14* (2006.01)
*B65G 33/32* (2006.01)
*G01N 27/22* (2006.01)

(52) U.S. Cl.
CPC ............ *B65G 43/02* (2013.01); *B65G 33/14* (2013.01); *B65G 33/32* (2013.01); *G01N 27/221* (2013.01); *G01N 27/223* (2013.01); *G01N 27/226* (2013.01); *B65G 2203/0208* (2013.01); *B65G 2203/042* (2013.01)

(58) Field of Classification Search
None
See application file for complete search history.

(56) References Cited

U.S. PATENT DOCUMENTS

| 3,675,367 A * | 7/1972 | Amburn | B65G 33/265 47/1.3 |
| 3,774,237 A * | 11/1973 | Hardway, Jr. | G01N 27/223 73/61.61 |
| 6,121,782 A * | 9/2000 | Adams | G01F 1/76 324/688 |
| 6,242,927 B1 * | 6/2001 | Adams | G01N 27/223 324/663 |
| 2011/0101997 A1 | 5/2011 | Gulbranson | |

FOREIGN PATENT DOCUMENTS

CN 111220662 A 6/2020

OTHER PUBLICATIONS

Fuchs et al. "Using Capacitive Sensing to Determine the Moisture Content of Wood Pellets—Investigations and Application" Internaltional Journal on Smart Sensing and Intelligent Systems, vol. 2, No. 2, Jun. 2009, 16 pgs.

* cited by examiner

*Primary Examiner* — Kavel Singh
(74) *Attorney, Agent, or Firm* — Dinsmore & Shohl LLP

(57) ABSTRACT

A screw conveyor system includes a conveyor body defining a conveyor cavity. The conveyor body includes an inlet for a conveyed material and an outlet. A screw blade is rotatably connected to the conveyor body via a shaft. The screw blade extends within the conveyor cavity between the inlet and the outlet. A hanger bearing support extends from an interior surface of the conveyor body into the conveyor cavity and a hanger bearing is attached to the hanger bearing support with the hanger bearing contacting the shaft to support the screw blade. A sensor support structure is connected to the hanger bearing support and the conveyor body. A capacitive sensor is attached to the sensor support structure and includes a first conductive plate and a second conductive plate spaced apart from one another to allow the conveyed material to travel between the first and second conductive plates.

12 Claims, 4 Drawing Sheets

RELATIVE-PERMITTIVITY-BASED ONLINE MONITORING SYSTEM FOR SCREW CONVEYORS

BACKGROUND

Field

The present specification generally relates to permittivity-based sensors. More particularly, the present specification relates to online permittivity-based sensors for integration into screw conveyors for detecting dielectric properties of a material being conveyed therethrough.

Technical Background

Screw conveyors are commonly used to convey a wide variety of particulate materials (e.g., grains, feed, various powders, etc.) within various production processes. For example, gas plants typically utilize screw conveyors in sulfur palletization plants as a medium to transfer sulfur powder prior to the powder's shipment to end users. Sulfur powders having relatively high moisture contents and tend to cohere with the screw conveyor, leading to accumulation within the screw conveyor and potential inhibition of the rotation of the screw conveyor's blades. Existence or abnormal levels of moisture collection within the screw conveyor thus have the potential to disrupt operation of the screw conveyor, leading to shipment delays and/or damage to the conveyor. Accordingly, plant operators typically schedule monthly cleaning activities to manually find and remove accumulations of powder. Such manual cleanings are time consuming, costly, and may be performed when they are not needed (e.g., over the course of a particular cleaning period, moisture may be successfully kept out of the screw conveyor or maintained at predefined acceptable levels, eliminating the need for a cleaning). It is estimated that screw conveyors conveying sulfur powder may trip three (3) times per year, with each trip causing at least a one (1) day shutdown to restore production. Depending on the material being conveyed, such conveyor trips may cost manufactures hundreds of thousands or millions of dollars per year.

Accordingly, a need exists for an online monitoring mechanism that identifies the need for screw conveyor cleanings to avoiding having unnecessary plant shut downs.

SUMMARY

According to an embodiment of the present disclosure, a screw conveyor system includes a conveyor body defining a conveyor cavity. The conveyor body includes an inlet for a conveyed material and an outlet for the conveyed material. A screw blade is rotatably connected to the conveyor body via a shaft. The screw blade extends within the conveyor cavity between the inlet and the outlet. A hanger bearing support extends from an interior surface of the conveyor body into the conveyor cavity. A hanger bearing attached to the hanger bearing support with the hanger bearing contacting the shaft to support the screw blade within the conveyor cavity. A sensor support structure is connected to the hanger bearing support and the conveyor body. A capacitive sensor is attached to the sensor support structure. The capacitive sensor includes a first conductive plate and a second conductive plate spaced apart from one another to allow the conveyed material to travel between the first and second conductive plates.

According to another embodiment of the present disclosure, an apparatus includes a screw conveyor including a conveyor body defining a conveyor cavity. The conveyor body comprises an inlet for a conveyed material and an outlet for the conveyed material. The apparatus includes a screw blade assembly comprising a screw blade rotatably supported within the conveyor cavity via a shaft. The apparatus includes a hanger bearing assembly comprising a hanger bearing support extending from an interior surface of the conveyor body to support a hanger bearing that rotatably supports the shaft. The apparatus includes a drive unit mechanically coupled to the shaft, wherein the drive unit is configured to rotate the shaft such that the screw blade rotates and pushes the conveyed material in a feed direction. The apparatus includes a capacitive sensor attached to the hanger bearing support via a sensor support structure extending between the conveyor body and the hanger bearing support. The capacitive sensor includes a parallel plate capacitor disposed within the conveyor cavity such that the conveyed material travels within the parallel plate capacitor when the conveyed material is pushed in the feed direction. The apparatus includes a measurement system including a voltage source configured to generate a potential difference between conductive plates of the parallel plate capacitor and an ammeter to measure a current flowing through conductors connected to the conductive plates.

According to another embodiment of the present disclosure, a method of detecting dielectric properties of a conveyed material includes rotating a shaft connected to a screw blade of a screw conveyor to push the conveyed material in a feed direction between two conductive plates of a capacitive sensor disposed within a conveyor cavity defined by a conveyor body. The capacitive sensor is attached to a hanger bearing support of the screw conveyor that is fixedly attached to the conveyor body. The method also includes applying a plurality of voltages between the two conductive plates while the conveyed material is disposed between the two conductive plates. The method also includes measuring a current for each of the plurality of voltages to determine a dielectric constant of the conveyed material.

Additional features and advantages of the processes and systems described herein will be set forth in the detailed description which follows, and in part will be readily apparent to those skilled in the art from that description or recognized by practicing the embodiments described herein, including the detailed description which follows, the claims, as well as the appended drawings.

It is to be understood that both the foregoing general description and the following detailed description describe various embodiments and are intended to provide an overview or framework for understanding the nature and character of the claimed subject matter. The accompanying drawings are included to provide a further understanding of the various embodiments, and are incorporated into and constitute a part of this specification. The drawings illustrate the various embodiments described herein, and together with the description serve to explain the principles and operations of the claimed subject matter.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, where like structure is indicated with like reference numerals and in which:

DETAILED DESCRIPTION

Figure 1A:
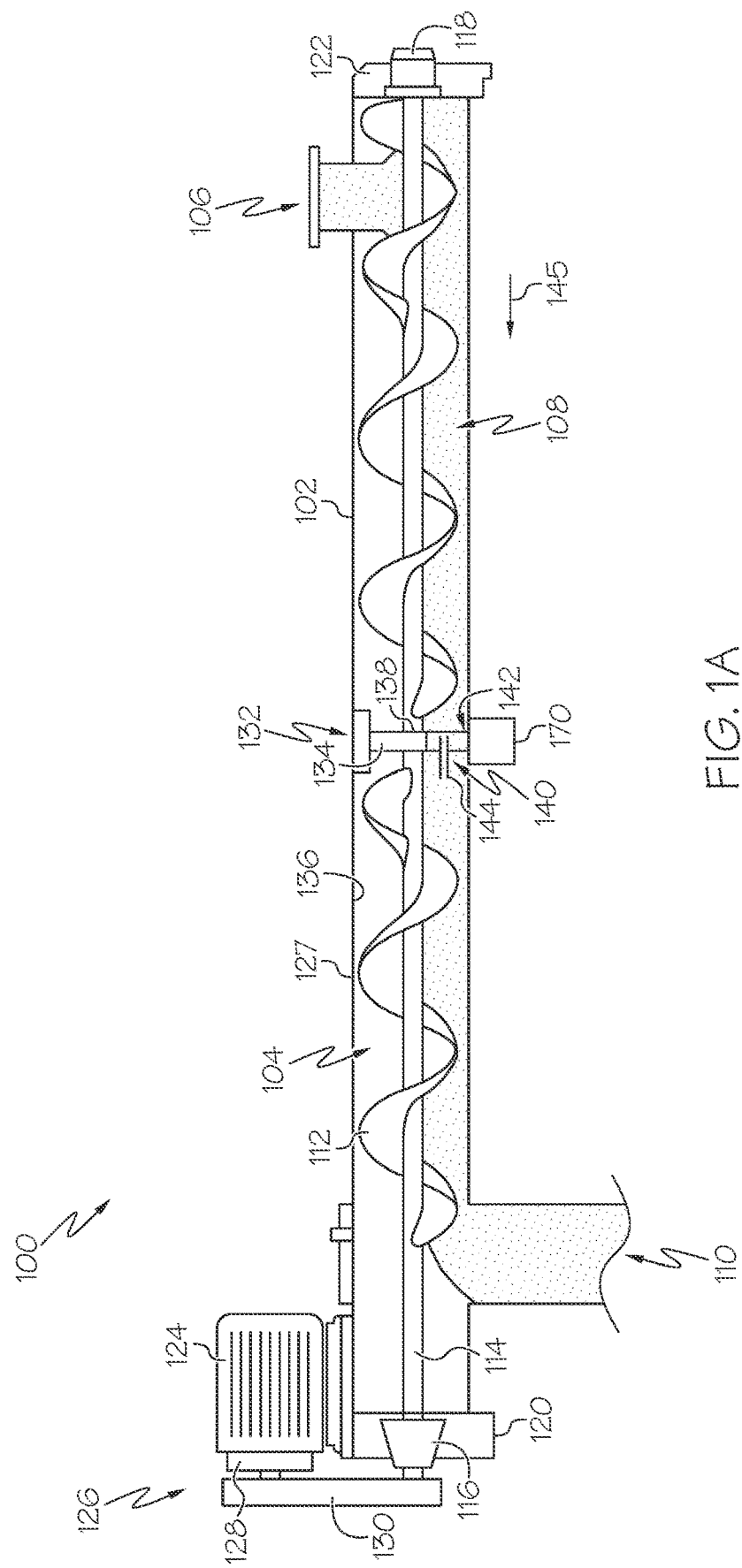
FIG. 1A schematically depicts a screw conveyor system, according to one or more embodiments described herein.

Reference will now be made in detail to embodiments of screw conveyor systems including capacitive sensors for in-situ monitoring of dielectric properties of materials being conveyed therethrough. In embodiments, a screw conveyor system in accordance with the present disclosure includes one or more capacitive sensors that are mounted to a hanger bearing assembly. For example, in embodiments, the screw conveyor systems include a conveyor body defining a conveyor cavity and a screw blade rotatably supported within the conveyor body via a shaft connected to the conveyor body. The shaft may be rotatably supported via a hanger bearing supported within the conveyor cavity by a hanger bearing support. The one or more capacitive sensors may be secured within the conveyor cavity between the screw blade and the conveyor body via a sensor support structure attached to the hanger bearing support. In embodiments, the capacitive sensor includes a pair of conductive plates that are supported by the sensor support structure such that the conductive plates extend parallel or substantially parallel to the shaft. When the screw blade is rotated (e.g., via a drive unit mechanically coupled to the shaft), a conveyed material in the conveyor cavity may be pushed in a feed direction between the conductive plates. While the conveyed material is disposed between the parallel plates, a plurality of potential differences may be generated between the pair of conductive plates (e.g., via a power supply conductively connected to the pair of conductive plates) and a plurality of current readings may be taken via an ammeter conductively connected to the pair of conductive plates for each of the plurality of voltages. Various dielectric properties (e.g., a dielectric constant) of the conveyed material may be determined from the plurality of current readings and used to estimate various properties of the conveyed material (e.g., moisture content, composition, etc.).

The capacitive sensors described herein beneficially allow in-situ characterization of the conveyed material without disrupting operation of the screw conveyor. The dielectric properties determined via the sensing methods described herein allow for the identification of material components of the conveyed material (e.g., moisture content) that may hinder operation of the screw conveyor system. Such knowledge may help in identifying a need for cleaning activities of the screw conveyor and avoid unneeded shutdowns.

Referring now to FIG. 1, a screw conveyor system 100 is schematically depicted, in accordance with an example embodiment. The screw conveyor system 100 includes a conveyor body 102 that defines a conveyor cavity 104. The conveyor body 102 includes an inlet 106 to facilitate a conveyed material 108 being introduced into the conveyor cavity 104 and an outlet 110 for the conveyed material 108. In embodiments, the outlet 110 is offset from the inlet 106 in a feed direction 145 and the conveyed material 108 is pushed in the feed direction 145 via the screw conveyor system 100 from the inlet 106 to the outlet 110. The screw conveyor system 100 may be situated within a wide variety of processes depending on the implementation such that the conveyed material 108 may take a wide variety of different forms. In embodiments, the conveyed material 108 may generally be a granular material (e.g., a powder, a seed, grains, animal feed, or other form of particulate matter). In embodiments, the conveyed material 108 includes sulfur powder and the screw conveyor system 100 is implemented within a sulfur palletization plant. For example, the screw conveyor system 100 may be used as a medium to transfer sulfur powder as part of the sulfur palletization process prior to shipment of end users.

While the conveyor body 102 is depicted to extend in a horizontal direction (e.g., such that the feed direction 145 is horizontal or extends substantially parallel to a surface upon which the conveyor body 102 is supported), it should be understood that the conveyor body 102 may have a variety of different orientations. For example, in embodiments, the conveyor body 102 is tilted relative to the depicted feed direction 145 such that gravity at least partially forces the conveyed material 108 towards the outlet 110 from the inlet 106. In embodiments, the conveyor body 102 is vertically orientated such that the feed direction 145 is parallel with gravity to provide gravitational assistance to the conveyed material 108. The present disclosure is not limited to the conveyor body 102 being in any particular orientation. In the depicted embodiment 102, the conveyor body 102 is substantially cylindrical-shaped and the conveyor cavity 104 is also substantially cylindrical-shaped. It should be understood that alternative shapes are envisioned for the conveyor body 102 and conveyor cavity 104 in various embodiments.

Referring still to FIG. 1A, the screw conveyor system 100 also includes a screw blade 112 that is rotatably connected to the conveyor body 102 via a shaft 114. The shaft 114 is rotatably connected to the conveyor body 102. In embodiments, for example, the shaft 114 is rotatably connected to the conveyor body 102 by one or more bearing assemblies disposed at one or more ends of the conveyor body 102. For example, in the depicted embodiment, the shaft 114 is rotatably connected to the conveyor body 102 via a first bearing assembly 116 disposed at a first end 120 of the conveyor body 102 and a second bearing assembly 118 disposed at a second end 122 of the conveyor body 102. The first and second bearing assemblies 116 and 118 may include any suitable type of bearing (e.g., roller bearing, ball bearing, air bearing, and the like) to facilitate rotation of the shaft 114 within the conveyor cavity 104.

The shaft 114 is mechanically connected to a drive unit 126 that rotates the shaft 114 within the conveyor cavity 104. In the depicted embodiment, the drive unit 126 includes an actuator 124 disposed on an exterior surface 127 of the conveyor body 102. The actuator 124 may include any suitable type of actuator (e.g., an internal combustion engine, an electric motor, a hydraulic motor) generating rotational energy from an input. In the depicted embodiment, the mechanical output of the actuator 124 is mechanically connected to the shaft 114 via a gearbox 128 and a transmission 130 that converts the rotational output of the actuator 124 to a suitable rotating speed for the screw blade 112. It should be appreciated that the depicted drive unit 126 is only one example and a variety of configurations for the drive unit 126 are contemplated and within the scope of the present disclosure. For example, in embodiments, rather than being disposed on the exterior surface 127, the actuator 124 may be supported (e.g., on the first end 120 or offset from the conveyor body 102) in-line with the shaft 114. In such embodiments, the transmission 130 may be omitted. As will be appreciated, the form and construction of the drive unit 126 may vary depending on the implementation and depend on the production process that the screw conveyor system 100 is being used in.

In embodiments, the screw blade 112 is fixedly attached to the shaft 114 and disposed within the conveyor cavity 104. In embodiments, the screw blade 112 includes a plurality of separate blade sections that are each individually connected to the shaft 114 (e.g., via welding or other suitable adherence technique). In embodiments, the shaft 114 comprises a plurality of sections associated with each one of the plurality of separate blade sections. In embodiments, the screw blade 112 and the shaft 114 form a single, integrated component.

As depicted in FIG. 1A, the screw blade 112 extends through the conveyor cavity 104 between the inlet 106 and the outlet 110. In the depicted embodiment, the screw blade 112 comprises an inlet end disposed proximate to the second end 122 of the conveyor body 102 and an outlet end disposed in alignment with the outlet 110. Actuation of the drive unit 126 may cause rotation of the shaft 114 and the screw blade 112. The screw blade 112 includes a helical shape and comprises surfaces that are slanted in the feed direction 145, such that rotation of the shaft 114 causes the screw blade 112 to push the conveyed material 108 in the feed direction 145 from the inlet 106 towards the outlet 110. The outlet end of the screw blade 112 being situated in alignment with the outlet 110 (e.g., in a direction perpendicular to the feed direction 145) beneficially facilitates the conveyed material 108 stopping at the outlet 110 and gravity feeding the conveyed material through the outlet 110 to a downstream portion of a production and/or transfer process for the conveyed material 108. It should be understood that the present disclosure is not limited to any particular physical structure of the screw blade 112 and that alternative structures for the screw blade 112 are contemplated and within the scope of the present disclosure. For example, in embodiments, rather than comprising a substantially continuous helical shape extending an entirety of the distance between the inlet 106 and the outlet 110 in the feed direction 145, the screw blade 112 may comprise a plurality of discrete sections. Moreover, in embodiments, the screw blade 112 may include portions that extend different radial distances outward from the shaft 114. In embodiments, the screw blade 112, the shaft 114, and one or more of the first and second bearing assemblies 116 and 118 are a screw blade assembly of the screw conveyor system 100 that is configured to push the conveyed material 108 between the inlet 106 and the outlet 110.

The screw conveyor system 100 further includes a hanger bearing assembly 132 supporting the shaft 114 within the conveyor cavity 104 between the first and second ends 120 and 122 of the conveyor body 102. The hanger bearing assembly 132 is depicted to include a hanger bearing 138 that is supported within the conveyor cavity 104 via a hanger bearing support 134 extending radially inward from an interior surface 136 of the conveyor body 102 (e.g., defining the conveyor cavity 104). In embodiments, the shaft 114 (or a section thereof) at least partially extends through an opening (not depicted) in the hanger bearing 138. In embodiments, the hanger bearing 138 includes a split roller bearing (or other suitable type of bearing) disposed in a housing. The hanger bearing 138 rotatably supports the shaft 114 and screw blade 112 within the conveyor cavity 104 to improve alignment of the shaft 114 and enhance the efficiency of the screw conveyor system 100. In embodiments, the hanger bearing support 134 includes bearing hangers, a threaded rod, or other suitable support structure for supporting the hanger bearing 138 at a desired position within the conveyor cavity 104. For example, in embodiments, the housing of the hanger bearing 138 includes extensions of the hanger bearings of the hanger bearing support 134 (e.g., the extensions may define an opening sized to receive the hanger bearing 138). In embodiments, the hanger bearing support 134 is centrally disposed within the conveyor cavity 104 and extends radially inward from the conveyor body 102 (e.g., radially between the interior surface 136 and the shaft 114 within the conveyor body 102).

Referring still to FIG. 1A, the conveyed material 108 has the potential to inhibit operation of the screw conveyor system 100. If the conveyed material 108 amalgamates on the interior surface 136 to a great enough extent, for example, the conveyed material 108 may impede rotation of the screw blade 112. As a result, the conveyed material 108 may completely stop operation of the screw conveyor system 100 by hindering operation of the drive unit 126, rendering it necessary to stop production of the conveyed material 108 and clean the conveyor cavity 104. Such stoppages in production are costly to manufacturers. Certain properties of the conveyed material 108 may render such accumulations more likely. For example, in embodiments where the conveyed material 108 includes sulfur powder, moisture content of the conveyed material 108 has been observed to render such stoppage-inducing accumulations more likely. In view of this, existing manufacturers may conduct regular cleanings of the conveyor body 102 to prevent accumulations of the conveyed material 108. Given the costliness of such cleanings, it is beneficial to only perform them when they are needed.

In view of the foregoing, the screw conveyor system 100 includes a capacitive sensor 140 that is supported within the conveyor cavity 104 by a sensor support structure 142. In embodiments, the sensor support structure 142 is connected to the hanger bearing support 134 and the conveyor body 102. In embodiments, the sensor support structure 142 extends between the interior surface 136 and the hanger bearing 138 or hanger bearing support 134. In embodiments, the sensor support structure 142 both structurally supports the capacitive sensor 140 within the conveyor cavity 104 and conductively connects conductive plates of the capacitive sensor 140 to a measurement system 170. Since the hanger bearing 138 and hanger bearing support 134 are stationary and securely mounted within the conveyor cavity 104, such components provide a useful connection point for the capacitive sensor 140. In embodiments, the capacitive sensor 140 is stationary within the conveyor cavity 104 to provide a consistent measurement point for dielectric properties of the conveyed material 108. In embodiments, the measurement system 170 is configured to provide voltages to the capacitive sensor 140 to create potential differences between conductive plates thereof in order to facilitate the measurements described herein.

The secure and stationary mounting of the capacitive sensor 140 within the conveyor cavity 104 via the hanger bearing support 134 and/or hanger bearing 138 beneficially facilitates the screw blade 112 forcing the conveyed material 108 through the capacitive sensor 140. In embodiments, for example, the capacitive sensor 140 includes a parallel plate capacitor 144 comprising a pair of conductive plates that are spaced apart from one another in a direction perpendicular or substantially perpendicular (e.g., within 10° of perpendicular) to the feed direction 145. Actuation of the drive unit 126 may force the conveyed material 108 between the pair of conductive plates. While the conveyed material 108 is between the conductive plates of the capacitive sensor 140, potential differences may be generated between the conductive plates and current readings may be taken by the measurement system 170 to determine dielectric properties of the conveyed material 108. As described herein, the dielectric properties of the conveyed material 108 may be used to determine compositional aspects (e.g., moisture content, chemical makeup) of the conveyed material 108 to determine if cleaning of the conveyor body 102 is needed. By relying on the output of the measurement system 170 generated via the capacitive sensor 140, cleanings may be performed on a more informed basis, eliminating unnecessary cleaning stoppages that are costly. The capacitive sensor 140, sensor support structure 142, and measurement system 170 will now be described in greater detail.

Figure 1B:
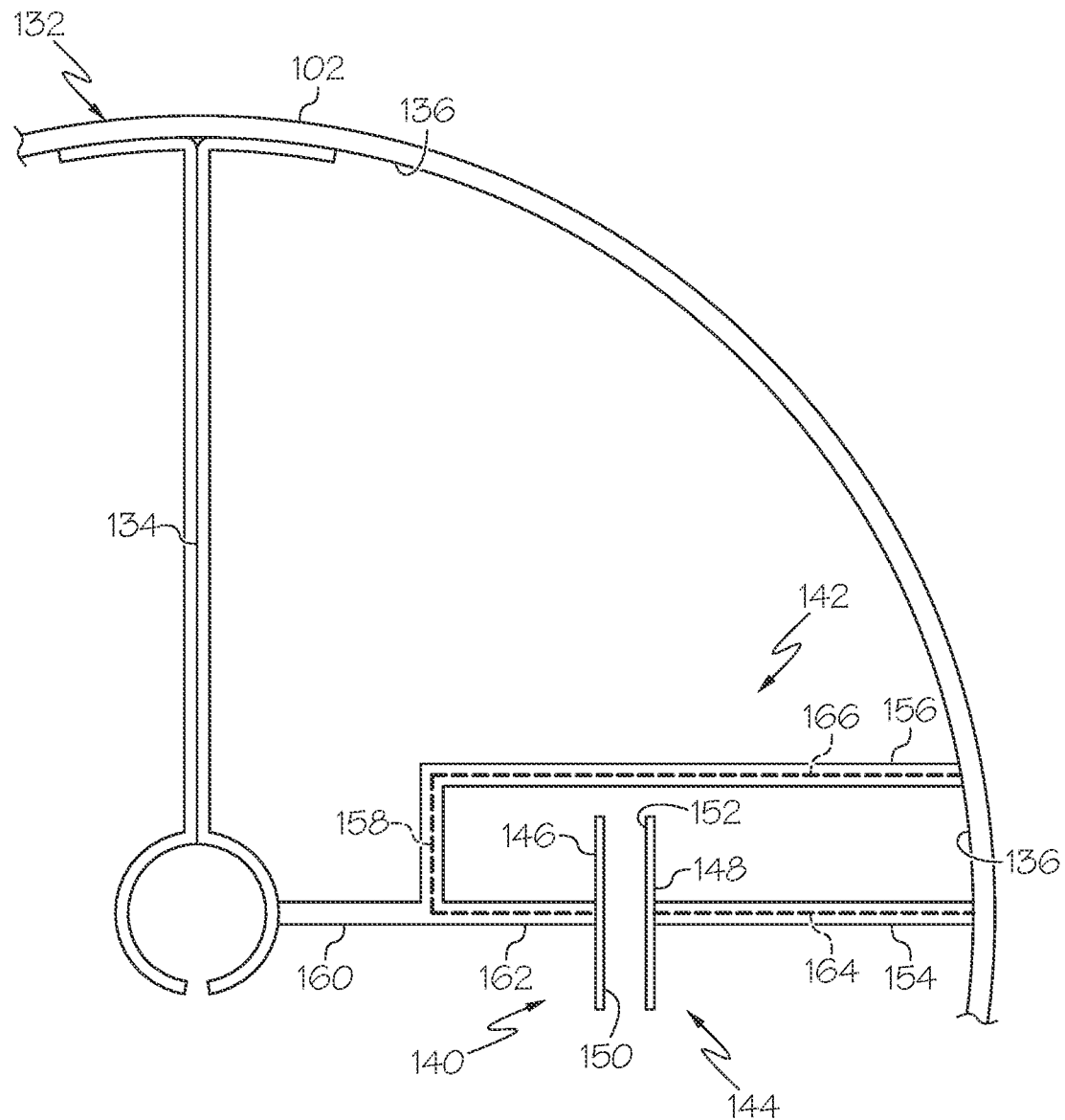
FIG. 1B schematically depicts a capacitive sensor and sensor support structure of the screw conveyor system of FIG. 1A, according to one or more embodiments described herein.

Referring now to FIG. 1B, the hanger bearing assembly 132, sensor support structure 142, and capacitive sensor 140 depicted in FIG. 1A are depicted in greater detail, according to an example embodiment. In the depicted embodiment, the hanger bearing support 134 comprises bearing hangers defining a support surface of the hanger bearing 138 (FIG. 1A). The hanger bearing support 134 extends radially inward from the conveyor body 102 to support the hanger bearing 138 within the conveyor cavity 104 (see FIG. 1A). The hanger bearing support and the sensor support structure 142 may extend at a plurality of different angles relative to one another depending on the configuration. It should be understood that alternative structures for the hanger bearing support 134 are contemplated and within the scope of the present disclosure. For example, in embodiments, the hanger bearing support 134 may include a threaded rod extending radially inward from the conveyor body 102 and a hanger bearing assembly (e.g., including a housing and a hanger bearing) may be connected to the threaded rod. The present disclosure is not limited to any particular structure for the hanger bearing support 134.

In the embodiment depicted in FIG. 1B, the parallel plate capacitor 144 of the capacitive sensor 140 includes a first conductive plate 148 and a second conductive plate 146 that are spaced apart from one another to allow the conveyed material 108 (see FIG. 1A) to travel between the first and second conductive plates 148 and 146. In embodiments, the first and second conductive plates 148 and 146 include interior surfaces 150 and 152 that extend parallel to one another. In embodiments, the interior surfaces 150 and 152 extend parallel or substantially parallel to the shaft 114 or the feed direction 145 (see FIG. 1A). When the interior surfaces 150 and 152 extend parallel to the feed direction 145, the cross-sectional areas of the first and second conductive plates 148 and 146 are beneficially minimized in a direction perpendicular to the feed direction 145, thereby reducing the impedance to flow of the conveyed material 108 caused by the capacitive sensor 140. It should be understood that alternative locations and orientations for the capacitive sensor 140 are contemplated and within the scope of the present disclosure. For example, in embodiments, the capacitive sensor 140 may be offset from the hanger bearing assembly 132 along the feed direction 145, although such embodiments may require larger sensor support structures 142, resulting in greater impedance to the flow of the conveyed material 108. In embodiments, the sensor support structure 142 extends radially outward from the shaft 114 at an angle to the hanger bearing support 134 (or a linear portion thereof). The angle may vary depending on the implementation. In FIG. 1A, the angle is depicted as approximately 180°, though the angle may vary (e.g., anywhere greater than or equal to 0° and less than or equal to 180°) in different implementations, so long as the capacitive sensor 140 is disposed within the conveyed material 108 (see FIG. 1A).

In the depicted embodiment, the sensor support structure 142 extends radially between the hanger bearing support 134 and the conveyor body 102. As described herein, the sensor support structure 142 may serve multiple functions of structurally supporting the capacitive sensor 140 within the conveyor cavity 104 and conductively connecting the first and second conductive plates 148 and 146 to the measurement system 170 (see FIG. 1A). Direct contact between conductive structures and the conveyed material 108 may result in adverse measurement influences. Accordingly, to avoid such contact between the conveyed material 108 and the conductive portions of the sensor support structure 142, the sensor support structure is depicted to include a first support line 154 extending between the conveyor body 102 and the first conductive plate 148 and a second support line 156 extending between the conveyor body 102 and the hanger bearing support 134.

In embodiments, the first and second support lines 154 and 156 are hollow structures. The first support line 154 being a hollow structure facilitates routing a first conductor 164 through the first support line 154 to provide a conductive connection point to connect the first conductive plate 148 to an exterior environment or surface of the conveyor body 102. The second support line 156 being a hollow structure facilitates routing a second conductor 166 through the second support line 156 to provide a conductive connection point to connect the second conductive plate 146 to an exterior environment or surface of the conveyor body 102. In embodiments, the first and second conductors 164 and 166 are conductively connected to the measurement system 170 described herein with respect to FIGS. 1A and 2 to facilitate providing voltages to the first and second conductive plates 148 and 146 and taking the various measurements described herein. In embodiments, the first and second conductors 164 and 166 are routed through openings in the conveyor body 102 to be attached to the measurement system 170. In embodiments, the first and second conductors 164 and 166 are connected to electrical connectors (not depicted) disposed within the conveyor body 102 to provide connection points for the measurement system 170.

The first and second support lines 154 and 156 may include hollow support tubes constructed of a suitable structural support material. In embodiments, the material out of which the first and second support lines 154 and 156 are constructed may vary depending on the conveyed material 108. In embodiments, the material out of which the first and second support lines 154 and 156 is non-conductive (e.g., an insulator) to avoid electromagnetic effects that may alter the measurements taken via the measurement system 170 described herein with respect to FIGS. 1A and 2. The first and second conductors 164 and 166 may be constructed of any suitable conductive material (e.g., copper) and take a variety of different forms (e.g., wires, plates, etc.) depending on the implementation. In embodiments, the first and second support lines 154 and 156 are structurally rigid such that the sensor support structure 142 maintains form despite being subjected to forces from the conveyed material 108. Such a configuration maintains the positioning of the parallel plate capacitor 144 to provide measurement consistency.

Figure 2:
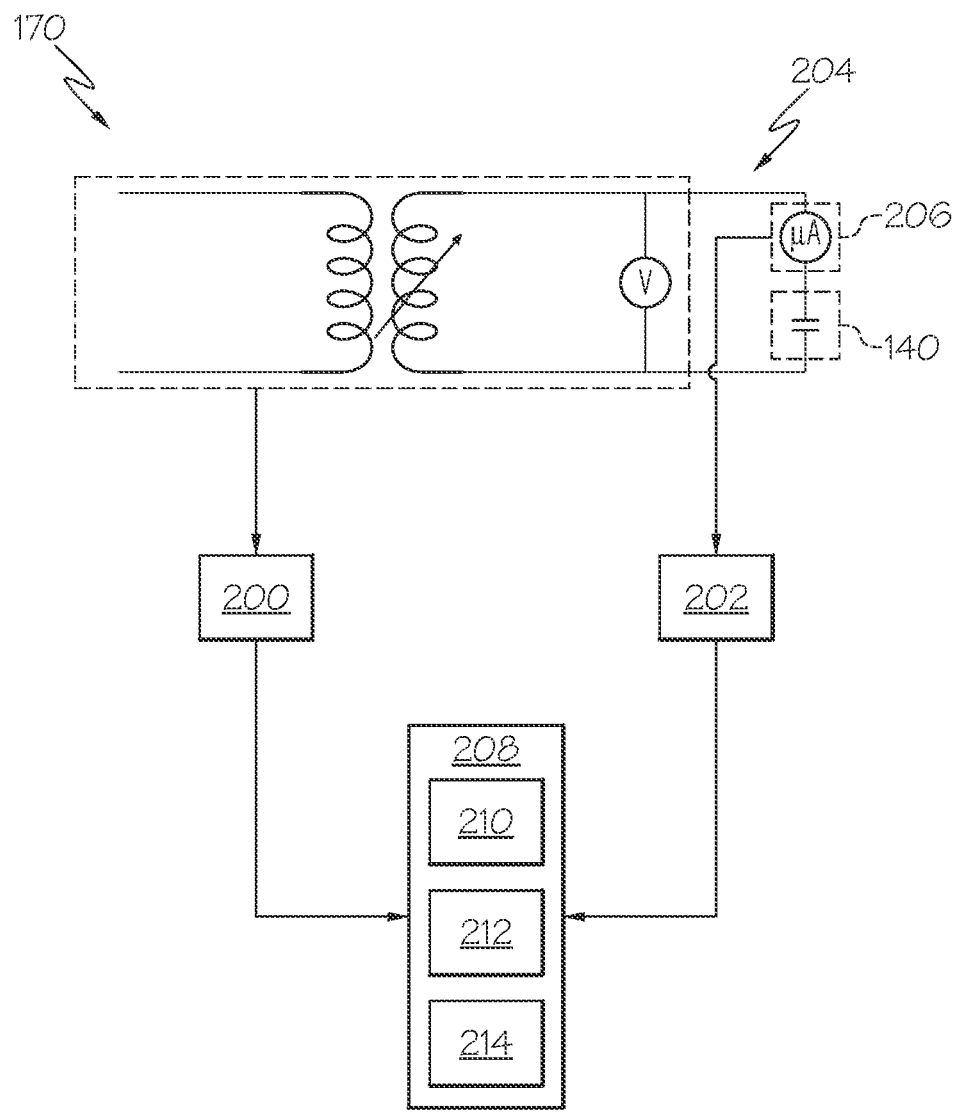
FIG. 2 schematically depicts a measurement system of the screw conveyor system of FIG. 1A, according to one or more embodiments described herein.

In embodiments, the first and second conductive plates 148 and 146 are conductively connected to the measurement system 170 described herein with respect to FIGS. 1A and 2 via separate connection points to facilitate generating a potential difference therebetween. As such, the first and second conductors 164 and 166 may not directly contact one another within the conveyor cavity 104 or prior to being connected to the measurement system 170. To provide such electrical separation between the first and second conductors 164 and 166, at least a portion of one of the first and second support lines 154 and 156 may be routed around at least a portion of the parallel plate capacitor 144. In the depicted embodiment, the second support line 156 turns from extending in a radial direction towards the hanger bearing support 134 to include a non-radial portion 158. In the depicted embodiment, the non-radial portion 158 extends parallel to the first and second conductive plates 148 and 146, though the non-radial portion 158 may extend in a variety of different directions depending on the implementation. After the non-radial portion 158, the second support line 156 branches off within the conveyor cavity 104 into a first portion 162 that is attached to the second conductive plate 146 and a second portion 160 that is attached to the hanger bearing support 134. The first portion 162 contains the second conductor 166 where the second conductor 166 attaches to the second conductive plate 146 and the second portion 160 is devoid of (or does not contain) the second conductor 166. Such a configuration beneficially avoids the second conductor 166 contacting any conductive components of the screw conveyor system 100.

As will be appreciated, the particular form of the sensor support structure 142 may vary depending on the structure, location, and orientation of the parallel plate capacitor 144. For example, in embodiments, the parallel plate capacitor 144 may be rotated by 90° about two axes relative to the orientation depicted in FIG. 1B such that the interior surfaces 150 and 152 are separated from one another in a direction parallel to the shaft 114 (see FIG. 1A). In such embodiments, both the first and second support lines 154 and 156 may be bent to include non-radial portions to facilitate connection at surfaces opposing the interior surfaces 150 and 152. Embodiments are also envisioned where the sensor support structure 142 is attached to the first and second conductive plates 148 and 146 at peripheral edges thereof rather than the outer surfaces depicted in FIG. 1B. Embodiments are also envisioned where a single support line branches off into separate portions to support the first and second conductive plates 148 and 146, or where the sensor support structure 142 comprises more than two support lines (e.g., 3, 4, 5, 6, 7, 8) to support each of the first and second conductive plates 148 and 146 at multiple locations. The size and/or shape of the sensor support structure 142 may depend on the size of the conveyor cavity 104 and various characteristics of the conveyed material 108 (e.g., density, rate at which the conveyed material 108 is fed through the conveyor body 102, etc.).

While the example screw conveyor system 100 described herein with respect to FIGS. 1A and 1B includes only a single capacitive sensor 140, it should be understood that embodiments including multiple capacitive sensors are also contemplated and within the scope of the present disclosure. In embodiments, the screw conveyor system 100 may include a plurality of capacitive sensors that attach to both the hanger bearing assembly 132 and the conveyor body 102. Each capacitive sensor of the plurality of capacitive sensors may have a structure that is similar to the capacitive sensor 140 described herein with respect to FIGS. 1A and 1B. Such a plurality of capacitive sensors may be disposed at the same position along the shaft 114 in some embodiments, or be offset from one another along the feed direction 145. In embodiments, the plurality of capacitive sensors are each individually supported by a sensor support structure similar to the sensor support structure 142 described with respect to FIG. 1B. In embodiments, subsets of the plurality of capacitive sensors, with each subset including more than one capacitive sensor, are supported by a single sensor support structure. That is, a single sensor support structure may be used to structurally support multiple capacitive sensors. Various combinations of sensor support structures and capacitive sensors are contemplated and within the scope of the present disclosure.

Referring now to FIG. 2, the measurement system 170 of the screw conveyor system 100 described herein with respect to FIGS. 1A and 1B is schematically depicted, according to an example embodiment. In the depicted embodiment, the measurement system 170 includes a power supply 200, a current measurement device 202, and a control system 208. In embodiments, the power supply 200 and the capacitive sensor 140 form a measurement circuit 204 (with the power supply 200 including the voltage source in the dashed lines). As shown, the power supply 200 is configured to generate a potential difference V across the capacitive sensor 140 (e.g., between the first and second conductive plates 148 and 146 described herein with respect to FIG. 1B) while the conveyed material 108 is disposed therein (e.g., between the first and second conductive plates 148 and 146). The current measurement device 202 is connected to one of the conductive plates of the capacitive sensor 140 at a current measurement point 206. As described herein, the current measurement device 202 may be used to take current readings while different potential differences V are applied between the conductive plates.

The capacitance C of the capacitive sensor 140 described herein is given by $$C = \frac{\varepsilon_o \varepsilon_r \times A}{d} \quad (1)$$

where $\varepsilon_0$ is the permittivity of free space (8,854×10$^{-12}$ F*m$^{-1}$), $\varepsilon_r$ is the permittivity of the conveyed material 108 (see FIG. 1A), A is the area of the first and second conductive plates 148 and 146 (see FIG. 1B), and d is the distance between the first and second conductive plates 148 and 146 in a direction perpendicular to the interior surfaces 150 and 152 (see FIG. 1B). The only unknown variables in equation 1 herein are the $\varepsilon_r$ and C.

Accordingly, the measurement circuit 204 utilizes a measurement sequence to solve for C and obtain an estimate of $\varepsilon_r$. For alternating current ("AC"), the voltage V between the conductive plates of the capacitive sensor 140 may be expressed as $$V = X_c I \quad (2)$$

where $X_c$ is the impedance of the capacitive sensor 140 and I is the current measured via the current measurement device 202. The impedance $I_c$ may also be expressed as $$X_c = \frac{1}{2\pi f C} \quad (3)$$

where f is the frequency of the AC voltage V supplied by the power supply 200 and C is the capacitance of the capacitive sensor 140. As such, by varying magnitude of the AC voltage V applied between the conductive plates of the capacitive sensor 140 and measuring the current I for each magnitude of the voltage, the capacitance C of the capacitive sensor 140 can be obtained. The obtained value for the capacitance C may then be inserted into equation 1 above to obtain the permittivity of the conveyed material 108 (i.e., $\varepsilon_r$ in equation 1 above). The value for $\varepsilon_r$ may be expressed as $$\varepsilon_r = \frac{C \times d}{\varepsilon_o \times A} \quad (4)$$

Accordingly, for a parallel plate capacitor having conductive plates of a particular area A and spacing d, the permittivity of the conveyed material 108 may be determined by taking a plurality of current readings by applying a plurality of potentially differences V between the parallel plates to determine the capacitance C and then using equation 4 to determine $\varepsilon_r$. For a particular example where the first and second conductive plates 148 and 146 comprise 5 cm×5 cm planar sheets (i.e., possessing an area of 25 cm$^2$) separated by a distance d of 1 cm, equation 4 becomes $$\varepsilon_r = \frac{C \times (10^{-2})}{8.854 \times 10^{-12} \times (5 \times 5 \times 10^{-4})} = 4.5177 \times 10^{11} \cdot C \quad (5)$$

As such, by measuring a plurality of current values via the current measurement device 202 (e.g., an ammeter) for a plurality of different AC voltages V between the conductive plates of the capacitive sensor 140 to determine the value C, the permittivity $\varepsilon_r$ of the conveyed material 108 can be quickly estimated. The permittivity value $\varepsilon_r$ for the conveyed material 108 may then be compared with various other values to characterize the conveyed material 108.

In embodiments, the power supply 200 and the current measurement device 202 are separate, portable components to facilitate performing the testing described herein using readily available equipment. For example, the power supply 200 may be a portable power supply that is connected to the conductive plates (e.g., via the first and second conductors 164 and 166) of the capacitive sensor 140 to generate an AC voltage having a magnitude V at a particular frequency f. While the power supply 200 is conductively connected to the capacitive sensor 140, the current measurement device 202 may be integrated into the measurement circuit 204 to take current readings for each voltage. The current readings may then be used to compute the capacitance C, which is plugged in an equation like equation 5 to determine $\varepsilon_r$.

As depicted in FIG. 2, in embodiments, the power supply 200 and the current measurement device 202 are communicably coupled to a control system 208. The control system 208 may control operation of the power supply 200 and the current measurement device 202 to perform the measurement sequence described herein in an automated fashion. As shown, the control system 208 includes a processor 210, a memory 212, and input/output ("I/O") hardware 214. While the control system 208 is shown to include a single processor 210, it should be appreciated that the control system 208 may include any number of processors depending on the implementation. The processor 210 can include any suitable processing device, such as a microprocessor, microcontroller, integrated circuit, logic device, and/or other suitable processing device. In embodiments, the processor 210 is a processing circuit (e.g., either a single processing circuit or a group processing circuit) that executes some or all of the machine-readable instructions from multiple modules of one or more non-transitory computer-readable mediums (e.g., the memory 212).

I/O hardware 214 may include at least one element to receive inputs from a user and/or provide results of the computations performed herein to other components (e.g., a display, a notification system, a network interface, or the like). In embodiments, I/O hardware 214 may include a basic input/output system (BIOS) that interacts with hardware of control system 208 and/or measurement system 170, device drivers, one or more operating systems, user applications, background services, background applications, and the like. In embodiments, the control system 208 includes a network interface (not depicted) including any suitable components for interfacing with one or more network(s), including for example, transmitters, receivers, ports, controllers, antennas, and/or other suitable components. Such a network interface may include and/or be configured to communicate with any wired or wireless networking hardware, including an antenna, a modem, a LAN port, a wireless fidelity (Wi-Fi) card, a WiMax card, a long term evolution (LTE) card, a ZigBee card, a Bluetooth chip, a USB card, mobile communications hardware, and/or other hardware for communicating with other networks and/or devices.

The memory 212 is communicatively coupled to the processor 210. As a non-limiting example, the memory 212 may include one or more non-transitory computer-readable medium that may be one of a shared memory circuit, dedicated memory circuit, or group memory circuit. Non-limiting examples of the memory include random access memory (including SRAM, DRAM, and/or other types of random access memory), read-only memory (ROM), flash memory, registers, compact discs (CD), digital versatile discs (DVD), and/or other types of storage components. Memory 212 may store instructions accessible to the processor 210 via an addressing scheme such that the processor 210 may access the memory 212 to execute the instructions in accordance with a program to perform any of the functions and operations described herein.

In embodiments, the memory 212 includes a measurement module configured to control the power supply 200 to generate a plurality of AC voltages having different magnitudes so as to generate a plurality of different potential differences V between the conductive plates of the capacitive sensor 140. The control system 208 (e.g., via the I/O hardware 214) may receive current readings from the current measurement device 202. The measurement module may cause the processor 210 to determine the capacitance value C for the capacitive sensor 140 based on the current readings and the magnitudes of the plurality of potentially differences V that were generated between the conductive plates of the capacitive sensor 140. The measurement module may also include instructions that cause the processor 210 to compute the permittivity value $\varepsilon_r$ of the conveyed material 108 using equation 4 herein. In embodiments, the measurement module is configured to cause the control system 208 to initiate such a measurement sequence after a predetermined time period (e.g., one minute, 30 minutes, one hour, six hours, one day, one week, etc.) has elapsed from a previous measurement of the permittivity value $\varepsilon_r$.

In embodiments, the memory 212 further includes analysis logic configured to determine a characteristic of the conveyed material 108 based on the obtained permittivity value $\varepsilon_r$. For example, in embodiments, the control system 208 may access a database of predetermined dielectric constants (e.g., associated with a set of known materials) and compare the obtained permittivity value $\varepsilon_r$ with the known dielectric constants to characterize the conveyed material 108. For example, in embodiments, the analysis logic may cause the processor 210 to determine a composition of the conveyed material 108 based on a comparison of the permittivity value $\varepsilon_r$ with one or more known dielectric constants.

The analysis carried out by the control system 208 may vary depending on the implementation and depending on particular conditions that are desirable to detect. For example, in embodiments where the conveyed material 108 is sulfur powder, it may be desirable to use the permittivity value $\varepsilon_r$ to estimate a moisture content of the conveyed material 108. For example, the particular manufacturing process in which the screw conveyor system 100 is used may render water the most likely constituent to enter the conveyor body 102 (see FIG. 1A). The presence of moisture may render the conveyed material 108 more likely to accumulate and impede operation of the screw conveyor system 100. Sulfur has a known dielectric constant (about 3.5 F/m), while water has a dielectric constant that varies as a function of temperature (the dielectric constant is about 48 F/m at 100° C. and approximately 80.4 F/m at room temperature). The contrast between the dielectric constants of water and sulfur render the moisture content of the conveyed material 108 discernable from the obtained dielectric permittivity value $\varepsilon_r$. For example, if the conveyed material was 72% by weight sulfur and 28% by weight water at room temperature, the measured permittivity value $\varepsilon_r$ would read approximately 25 F/m. As such, in situations where there are unlikely to be other chemical constituents introduced into the conveyed material 108 and where the temperature of any water introduced into the conveyed material is known, the moisture content of the conveyed material 108 may readily be deduced from the obtained permittivity value $\varepsilon_r$.

In embodiments, the estimated moisture content (or content of any other chemical constituent desired to be identified via the measurement processes described herein) may be compared to one or more thresholds to provide a cleaning notification or to control a cleaning process. For example, in the preceding example where the conveyed material 108 includes sulfur powder, the estimated moisture content may be compared to a threshold. The threshold may be predetermined experimentally to be a value likely to result in significant accumulation of the conveyed material 108 in the conveyor body 102 (see FIG. 1A). In embodiments, if the estimated moisture content exceeds the threshold, the control system 208 may provide a cleaning notification. The cleaning notification may take a variety of forms depending on the implementation. For example, in embodiments, the cleaning notification includes an alert presented via a display of the control system 208. In embodiments, the cleaning notification includes a notification (e.g., a push notification or the like) or message transmitted to an external computing device over a network. This way, an operator of the screw conveyor system 100 (see FIG. 1A) may only perform cleanings of the conveyor body 102 when measurements taken by the capacitive sensor 140 confirm a likelihood of accumulation. Costs associated with unnecessary shutdowns are thus avoided.

It should be understood that the measurement system 170 depicted in FIG. 2 may be used in a variety of different ways to detect or estimate a number of different properties of the conveyed material 108. For example, in embodiments, the control system 208 analyzes the estimated permittivity values $\varepsilon_r$ over time and preforms a trend analysis to determine whether a cleaning is needed. That is, a cleaning notification may not be generated in response to a single permittivity value $\varepsilon_r$, but rather a plurality of estimated permittivity values $\varepsilon_r$ over a time period (e.g., a percentage increase in permittivity value $\varepsilon_r$ over a predetermined time period may trigger a cleaning notification). In embodiments, the control system 208 maintains a database of previous measurements and compares the latest permittivity value $\varepsilon_r$ with previous measurements to estimate various qualities of the conveyed material 108. The present disclosure is not limited to any particular use of the estimated dielectric properties of the conveyed material 108.

Figure 3:
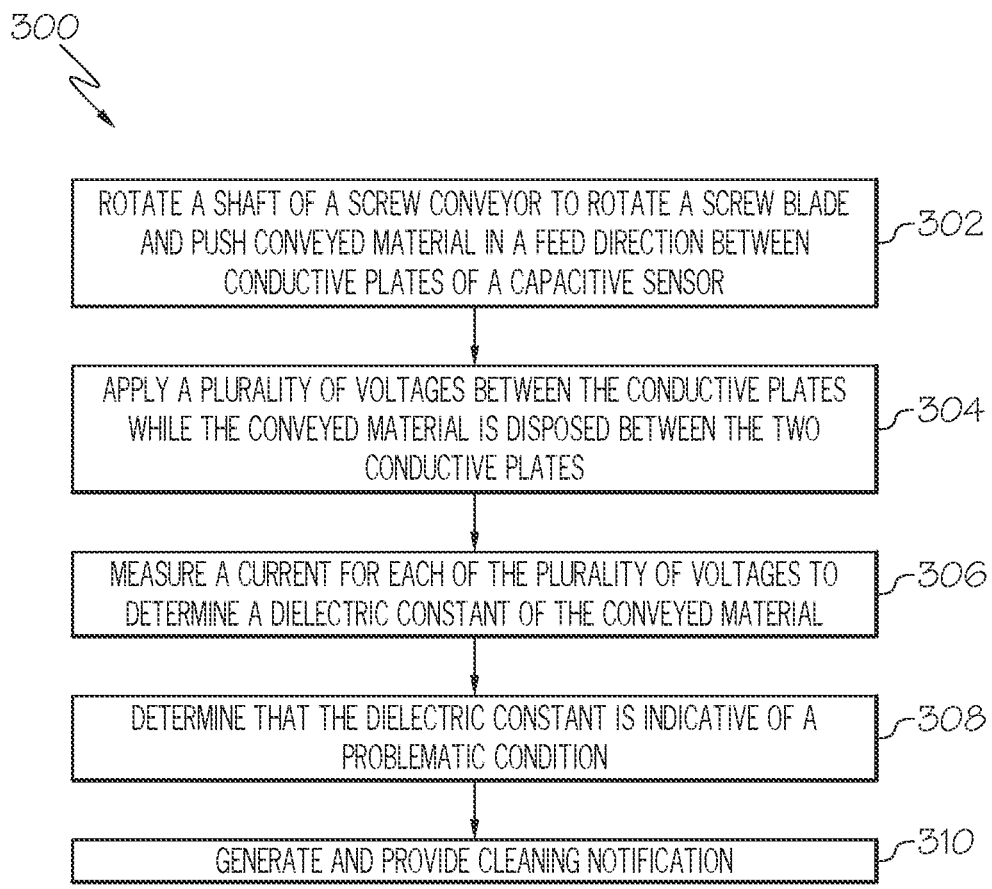
FIG. 3 schematically depicts a flow diagram of a method of determining a dielectric constant of a material being conveyed through a screw conveyor and providing a cleaning notification based on the dielectric constant, according to one or more embodiments described herein.

Referring now to FIG. 3 a flow diagram of a method 300 of determining a dielectric constant of a material being conveyed through a screw conveyor is shown, according to an example embodiment. In embodiments, the method 300 may be performed via the screw conveyor system 100 described herein with respect to FIGS. 1A, 1B, and 2 to determine a dielectric constant of the conveyed material 108. Accordingly, reference will be made to various components depicted in FIGS. 1A, 1B, and 2 to aid in the description of the method 300. It should be understood that the method 300 may be performed by systems other than those described herein and that the method is not limited to the particular context of the forthcoming description thereof.

With reference to FIGS. 1A-3, at block 302, the shaft 114 of the screw conveyor system 100 is rotated to rotate the screw blade 112 and push the conveyed material 108 in the feed direction 145. As described herein, the screw conveyor system 100 includes a capacitive sensor 140 including the first and second conductive plates 148 and 146 that are spaced apart from one another. The capacitive sensor 140 is disposed within the conveyor cavity 104 such that, when the shaft 114 is rotated via the drive unit 126, the screw blade 112 pushes the conveyed material 108 in the feed direction 145 between the first and second conductive plates 148 and 146. At block 304, while the conveyed material 108 is disposed between the first and second conductive plates 148 and 146, the measurement system 170 (e.g., via the power supply 200) applies a plurality of voltages between the first and second conductive plates 148 and 146. In embodiments, the power supply 200 is manually controlled by a user to generate a plurality of alternating current potential differences having a plurality of different magnitudes V at a frequency f. In embodiments, the power supply 200 is automatically controlled via the control system 208, which may include control logic to generate a predetermined set of potential differences between the first and second conductive plates 148 and 146.

At block 306, the current measurement device 202 is used to measure a current for each of the plurality of voltages applied to the capacitive sensor 140 at block 304. As described herein with respect to equations 2 and 3, the plurality of current values measured may be used to obtain the impedance of the capacitive sensor 140, which may be used to calculate the capacitance and then the permittivity value $\varepsilon_r$ of the conveyed material 108. At block 308, via the measurement system 170, it is determined that the dielectric constant measured at block 306 is indicative of a problematic condition. For example, in embodiments, the permittivity value $\varepsilon_r$ may be compared to a threshold and, if the permittivity value $\varepsilon_r$ is greater than the threshold, this may serve as an indication of a problematic condition. As described above, if the permittivity value $\varepsilon_r$ is greater than a threshold, such a condition may indicate a high moisture content and likely accumulation of the conveyed material. In embodiments, the determination that the dielectric constant is indicative of the problematic condition is performed manually by a user. In embodiments, the determination is automatically performed via the control system 208 comparing the permittivity value $\varepsilon_r$ to a threshold or performing one or more additional operations on the permittivity value $\varepsilon_r$. It should be understood that the determination that the dielectric constant is indicative of a problematic condition may take a variety of different forms depending on the implementation. For example, in embodiments, the permittivity value $\varepsilon_r$ being less than a threshold may be indicative of a problematic condition. In embodiments, trends in the permittivity value $\varepsilon_r$ (e.g., percentage of increases or decreases over predetermined time periods) are indicative of the problematic condition. Moreover, the problematic condition itself may take a variety of forms. While the examples described herein relate to an estimation of the moisture content of the conveyed material 108, it should be understood that the methods described herein may be used to detect or identify any constituent having a predetermined dielectric constant value.

At block 310, the control system 208 generates and provides a cleaning notification. In embodiments, for example, in response to a determination that the permittivity value is indicative of a problematic condition, the control system 208 provides the cleaning notification. The cleaning notification may take a variety of forms, including, but not limited to, an alert display, a push notification, a message conveyed over a network, a sound, or any other detectable stimulus. The cleaning notifications provided via the measurement system 170 described herein beneficially notify manufacturers when shutdowns are absolutely necessary for cleaning, thereby avoiding unnecessary shutdowns and the costs associated therewith.

In view of the foregoing description, it should be understood that integrating a capacitive sensor into screw conveyors using the sensor support structures described herein beneficially permit online permittivity-based measurements of conveyed materials in real time. Such measurements beneficially enable determination of when a cleaning of a particular screw conveyor is needed. Hanger bearing assemblies beneficially provide a stationary connection point for the sensor support structures described herein that are centrally situated within the screw conveyors to facilitate measurement of a portion of the conveyed material that is representative of the remainder thereof that is conveyed through the screw conveyor. By utilizing sensor support structures including non-conductive support lines having conductors extending therethrough to conductively connect the capacitive sensors described herein to measurement systems, conductive contact with the conveyed material is beneficially avoided, improving measurement quality.

As used herein, the term "about" means that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art. When the term "about" is used in describing a value or an end-point of a range, the specific value or end-point referred to is included. Whether or not a numerical value or end-point of a range in the specification recites "about," two embodiments are described: one modified by "about," and one not modified by "about." It will be further understood that the endpoints of each of the ranges are significant both in relation to the other endpoint, and independently of the other endpoint.

Directional terms as used herein—for example up, down, right, left, front, back, top, bottom—are made only with reference to the figures as drawn and are not intended to imply absolute orientation.

Unless otherwise expressly stated, it is in no way intended that any method set forth herein be construed as requiring that its steps be performed in a specific order, nor that with any apparatus specific orientations be required. Accordingly, where a method claim does not actually recite an order to be followed by its steps, or that any apparatus claim does not actually recite an order or orientation to individual components, or it is not otherwise specifically stated in the claims or description that the steps are to be limited to a specific order, or that a specific order or orientation to components of an apparatus is not recited, it is in no way intended that an order or orientation be inferred, in any respect. This holds for any possible non-express basis for interpretation, including: matters of logic with respect to arrangement of steps, operational flow, order of components, or orientation of components; plain meaning derived from grammatical organization or punctuation, and; the number or type of embodiments described in the specification.

As used herein, the singular forms "a," "an" and "the" include plural referents unless the context clearly dictates otherwise. Thus, for example, reference to "a" component includes aspects having two or more such components, unless the context clearly indicates otherwise.

It will be apparent to those skilled in the art that various modifications and variations can be made to the embodiments described herein without departing from the spirit and scope of the claimed subject matter. Thus, it is intended that the specification cover the modifications and variations of the various embodiments described herein provided such modifications and variations come within the scope of the appended claims and their equivalents.

What is claimed is:

1. A screw conveyor system comprising:
    a conveyor body defining a conveyor cavity, wherein the conveyor body comprises an inlet for a conveyed material and an outlet for the conveyed material;
    a screw blade rotatably connected to the conveyor body via a shaft, wherein the screw blade extends within the conveyor cavity between the inlet and the outlet;
    a hanger bearing support extending from an interior surface of the conveyor body into the conveyor cavity;
    a hanger bearing attached to the hanger bearing support, the hanger bearing contacting the shaft to support the screw blade within the conveyor cavity;
    a sensor support structure connected to the hanger bearing support and the conveyor body; and
    a capacitive sensor attached to the sensor support structure, wherein the capacitive sensor comprises a first conductive plate and a second conductive plate spaced apart from one another to allow the conveyed material to travel between the first and second conductive plates, wherein the sensor support structure comprises:
        a first support line extending between the conveyor body and the first conductive plate;
        a first conductor extending through the first support line to conductively connect the first conductive plate to an exterior surface of the conveyor body;
        a second support line extending between the conveyor body and the hanger bearing support; and
        a second conductor extending through the second support line to conductively connect the second conductive plate to the exterior surface, wherein the second support line branches off within the conveyor cavity into a first portion that is attached to the second conductive plate and contains the second conductor and a second portion that is attached to the hanger bearing support.

2. The screw conveyor system of claim 1, wherein the first and second conductive plates extend parallel to one another.

3. The screw conveyor system of claim 2, wherein the first and second conductive plates comprise inner surfaces that face one another and extend parallel to the shaft.

4. The screw conveyor system of claim 1, wherein the hanger bearing support is centrally disposed within the conveyor cavity and extends radially inward from the conveyor body.

5. The screw conveyor system of claim 4, wherein the sensor support structure extends radially between the hanger bearing support and the conveyor body.

6. The screw conveyor system of claim 1, wherein the second portion is devoid of conductive material.

7. The screw conveyor system of claim 1, further comprising a power supply conductively connected to the first and second conductive plates, wherein the power supply is configured to generate a potential difference between the first and second conductive plates.

8. The screw conveyor system of claim 7, wherein the power supply is configured to generate an alternating current voltage that is applied between the first and second conductive plates.

9. The screw conveyor system of claim 7, further comprising an ammeter to measure a current between the first and second conductive plates.

10. An apparatus comprising:
a screw conveyor comprising:
   a conveyor body defining a conveyor cavity, wherein the conveyor body comprises an inlet for a conveyed material and an outlet for the conveyed material;
   a screw blade assembly comprising a screw blade rotatably supported within the conveyor cavity via a shaft;
   a hanger bearing assembly comprising a hanger bearing support extending from an interior surface of the conveyor body to support a hanger bearing that rotatably supports the shaft;
   a drive unit mechanically coupled to the shaft, wherein the drive unit is configured to rotate the shaft such that the screw blade rotates and pushes the conveyed material in a feed direction;
   a capacitive sensor attached to the hanger bearing support via a sensor support structure extending between the conveyor body and the hanger bearing support, the capacitive sensor comprising a parallel plate capacitor disposed within the conveyor cavity such that the conveyed material travels within the parallel plate capacitor when the conveyed material is pushed in the feed direction, wherein the sensor support structure comprises:
      a first support line extending between the conveyor body and a first conductive plate of the conductive plates;
      a first conductor extending through the first support line to conductively connect the first conductive plate to an exterior surface of the conveyor body;
      a second support line extending between the conveyor body and the hanger bearing support; and
      a second conductor extending through the second support line to conductively connect a second conductive plate of the conductive plates to the exterior surface, wherein the second support line branches off within the conveyor cavity into a first portion that is attached to the second conductive plate and contains the second conductor and a second portion that is attached to the hanger bearing support; and
a measurement system comprising:
   a voltage source configured to generate a potential difference between conductive plates of the parallel plate capacitor; and
   an ammeter to measure a current flowing through conductors connected to the conductive plates.

11. The apparatus of claim 10, wherein the first and second conductive plates comprise inner surfaces that face one another and extend parallel to the shaft.

12. The apparatus of claim 10, wherein the voltage source and the ammeter are conductively connected to the conductive plates via the first and second conductors at the exterior surface.

* * * * *